(12) United States Patent
Skovlund

(10) Patent No.: US 6,503,208 B1
(45) Date of Patent: Jan. 7, 2003

(54) METHOD AND APPARATUS FOR THE MEASUREMENT OF INTRA-ABDOMINAL PRESSURE

(75) Inventor: Erik Skovlund, Charlottenlund (DK)

(73) Assignee: Holtech Medical (DK)

( * ) Notice: Subject to any disclaimer, the term of this patent is extended or adjusted under 35 U.S.C. 154(b) by 138 days.

(21) Appl. No.: 09/730,276

(22) Filed: Dec. 5, 2000

(51) Int. Cl.⁷ .................................................. A61B 5/00
(52) U.S. Cl. ....................................... 600/561; 604/317
(58) Field of Search ........................ 600/561, 403–405, 600/587, 573, 581, 593; 604/317–328; 73/1.57–1.73, 700–756

(56) References Cited

U.S. PATENT DOCUMENTS

| | | | |
|---|---|---|---|
| 3,980,082 A | 9/1976 | Miller | 128/214 |
| 4,170,224 A | 10/1979 | Garrett et al. | 128/748 |
| 4,184,484 A | 1/1980 | Wright et al. | 128/748 |
| 4,217,911 A | 8/1980 | Layton | 128/748 |
| 4,696,672 A | 9/1987 | Mochizuki et al. | 604/128 |
| 4,711,248 A | 12/1987 | Steuer et al. | 128/748 |
| 4,727,887 A | 3/1988 | Haber | 128/748 |
| 4,790,328 A | 12/1988 | Young | 128/748 |
| 4,841,984 A | 6/1989 | Armeniades et al. | 128/645 |
| 5,211,642 A | 5/1993 | Clendenning | 605/410 |

FOREIGN PATENT DOCUMENTS

GB 2151139 7/1985

OTHER PUBLICATIONS

"Bedside measurement of intra-abdominal pressure (IAP) via an indwelling naso-gastric tube: clinical validation of the technique", Collee et al., Intensive Care Medicine, 1993, pp. 478–480.
Revision of the original Kron method for intravascular pressure measurement by Cheatha and Safcsak, Intensive Care Medicine, Dec. 1999, p. 1454.
"The Measurement of Intra-abdominal Pressure as a Criterion for Abdominal Re-exploration", Kron et al., Department of Surgery, University of Virginia Medical Center, vol. 199, No. 1, Jun. 15, 1983, pp. 28–30.

Primary Examiner—Max F. Hindenburg
Assistant Examiner—Pamela L. Wingood
(74) Attorney, Agent, or Firm—Andrus, Sceales, Starke & Sawall, LLP

(57) ABSTRACT

A method and apparatus for measuring the intra-abdominal pressure within a patient. A reservoir is positioned between a drainage catheter (e.g. a urinary catheter or naso-gastric tube) and a collection container for the fluid being drained from the patient's body. The reservoir defines a constant volume and receives the withdrawn fluid through a manometer tube having a series of markings. The reservoir includes an air vent that ensures that the volume of fluid in the reservoir is held at atmospheric pressure when the reservoir is raised above the patient. When the reservoir is raised to a predetermined measurement height above the patient, the volume of fluid in the reservoir is returned to the patient. The height of the liquid column within the manometer tube provides a direct indication of the intra-abdominal pressure of the patient.

21 Claims, 3 Drawing Sheets

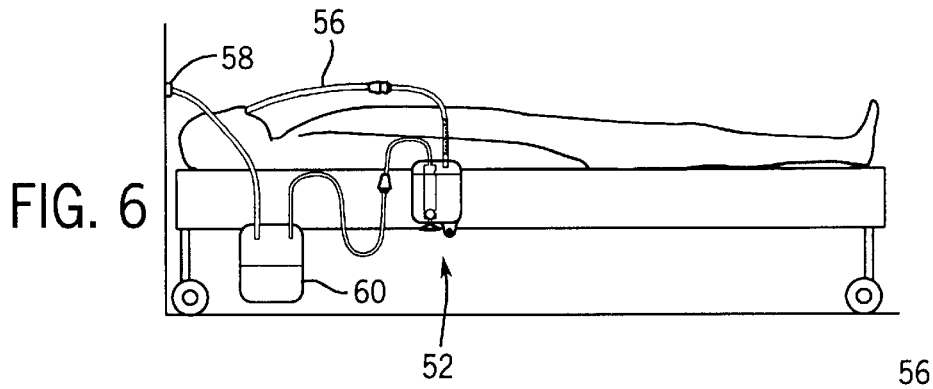
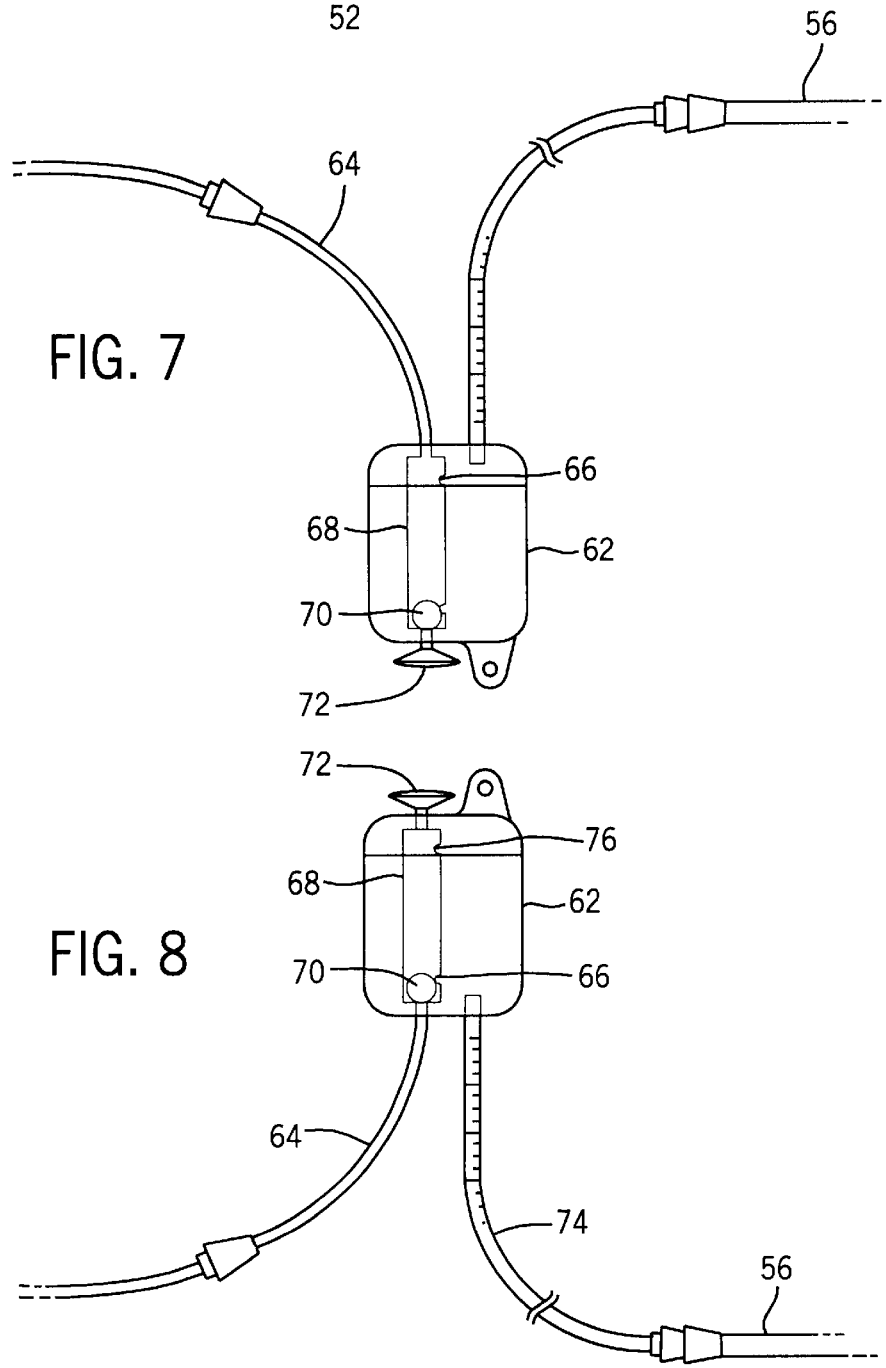

METHOD AND APPARATUS FOR THE MEASUREMENT OF INTRA-ABDOMINAL PRESSURE

BACKGROUND OF THE INVENTION

The present invention relates to an apparatus and method that are useful in the measurement of the pressure within the human body abdominal cavity or hollow viscous organ contained in the abdominal cavity. More specifically, the present invention relates to an apparatus and method that utilizes the patient's own bodily fluid collected within a reservoir to measure the intra-abdominal pressure.

The measurement of intra-abdominal (or intra-visceral) pressure is routinely made in the clinical management of critically ill patients, or patients undergoing major surgery. Typically, the urinary bladder is the preferred site for the pressure measurement, but other hollow organs, such as the stomach, may be used as well.

Urinary bladder pressure is presently measured by connecting a pressure recording device to the patient's urinary (Foley) catheter, which empties the bladder into a drainage container. Under the prior art method, the drainage container tube is clamped and 50 cc of sterile saline is infused into the bladder from a syringe by a needle inserted into the catheter's sampling port. After infusion, the pressure in the bladder is recorded using the level of the pubic bone (symphysis pubis) as the zero pressure reference. This method is both time-consuming and presents a risk for bladder infection because the closed sterile tubing may be contaminated by the introduction of the needle when inserting the supply of saline.

SUMMARY OF THE INVENTION

The present invention relates to a method and apparatus for determining the intra-abdominal pressure of a patient. Specifically, the present invention relates to an apparatus and method that utilizes a stored quantity of the patient's own bodily fluid to determine the intra-abdominal pressure within the patient.

In the first embodiment of the invention, the pressure measuring apparatus includes a fluid reservoir that is positioned between a urinary catheter inserted into the patient and the collection container for urine withdrawn from the patient through the urinary catheter. The reservoir has a predetermined internal volume that stores a predetermined amount of urine within the reservoir. An outlet opening within the reservoir allows excess urine to drain into the collection chamber. The reservoir is connected to the urinary catheter by a manometer tube having a series of indicator marks, including a zero marking.

During pressure determination, the reservoir is elevated to a measurement height above the patient until the zero marking on the manometer tube is generally level with the pubic bone of the patient. A filtered air vent at the top of the reservoir provides atmospheric pressure inside of the reservoir. As the reservoir is elevated to the measurement height, the internal supply of the patient's own urine within the reservoir flows through the manometer tube and the urinary catheter back into the bladder of the patient. Once the reservoir has been elevated such that the zero marking on the manometer tube is level with the pubic bone, the height of the liquid column contained within the manometer tube provides a direct indication of the intra-abdominal pressure of the patient.

Alternatively, the manometer tube extending between the reservoir and the urinary catheter can be replaced by a simple, unmarked transparent inlet tube extending between the reservoir and the urinary catheter. A measuring tape including a series of indicator marks is attached to the bottom of the reservoir and the opposite end of the measuring tape is fixed relative to the patient's bed. The length of the measuring tape is fixed such that a zero marking on the measuring tape corresponds to the level of the patient's pubic bone when the patient is in a supine position. The measurement height of the reservoir is thus dictated by the length of the measuring tape. When the reservoir is at its prescribed measurement height, the height of the liquid column within the transparent inlet tube is measured along the indicator lines on the measuring tape. The height of the liquid column directly measures the intra-abdominal pressure of the patient.

In a second embodiment of the invention, the reservoir is positioned between a naso-gastric tube and a supply of suction used to withdraw fluid from a patient's stomach. During normal draining situations, the reservoir is in an inverted position that allows suction to withdraw fluid from the patient's stomach. A ball within the reservoir closes the air vent to the reservoir when the reservoir is in its inverted position.

Measurement of the patient's intra-abdominal pressure through the naso-gastric tube is done by first placing the reservoir in an upright position. In the upright position, the ball within the reservoir closes the outlet opening to the supply of suction to prevent the patient's stored stomach fluid from leaving the reservoir through the suction tube while allowing air to enter the reservoir through the filtered vent. The reservoir is then elevated in the manner described previously such that the patient's own stomach fluid flows back into the patient's stomach.. The height of the stored stomach fluid within the manometer tube provides a direct indication of the intra-abdominal pressure of the patient.

Various other features, objects and advantages of the invention will be made apparent from the following description taken together with the drawings.

BRIEF DESCRIPTION OF THE DRAWINGS

The drawings illustrate the best mode presently contemplated of carrying out the invention.

In the drawings:

FIG. 6 is an illustration of a second embodiment of the intra-abdominal pressure measuring device of the present invention as used with a naso-gastric tube;

FIG. 7 is an illustration of the second embodiment of the intra-abdominal pressure measuring device in its inverted, non-operative position; and FIG. 8 is an illustration of the second embodiment of the intra-abdominal pressure measuring device in its upright, pressure measuring position.

DETAILED DESCRIPTION OF THE INVENTION

Figure 1:
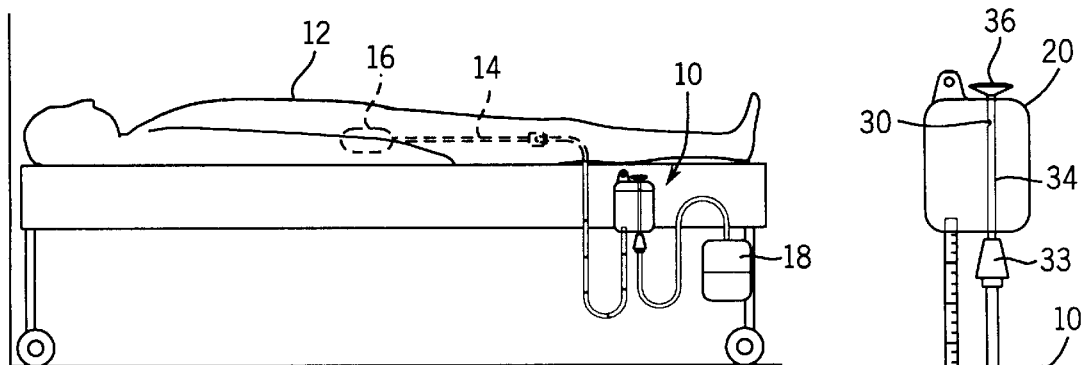
FIG. 1 is an illustration of the intra-abdominal pressure measuring device of the present invention.

Referring first to FIG. 1, thereshown is the intra-abdominal pressure measuring apparatus 10 of the present invention as being used on a patient 12 in a post-operative environment. As illustrated in FIG. 1, the patient 12 is in a supine position with a catheter, such as a urinary (Foley) catheter 14, positioned to drain the patient's bladder 16 into a collection container 18.

Figure 2:
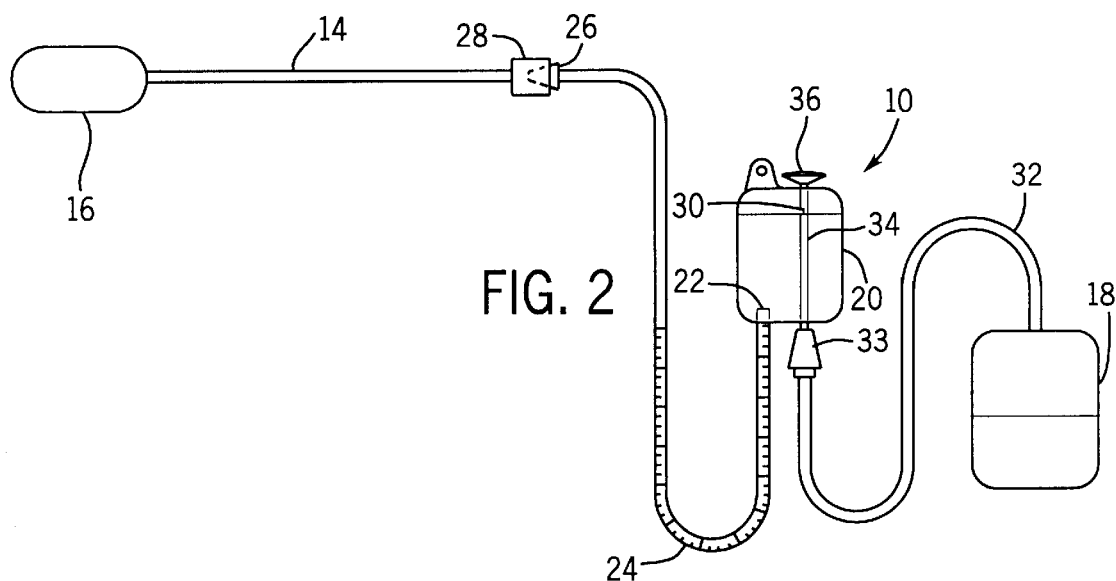
FIG. 2 is a magnified illustration of the intra-abdominal pressure measuring device of the present invention.

Referring now to FIG. 2, the pressure measuring apparatus 10 of the present invention includes a reservoir 20 positioned between the urinary catheter 14 and the collection container 18. The reservoir 20 is positioned below the patient's bladder 16 and includes an inlet opening 22 that receives a first end of a manometer tube 24. The manometer tube 24 is a transparent inlet tube that includes a series of measurement markings that are utilized in the pressure measurement process to be detailed below. In the preferred embodiment of the invention, the measurement markings are calibrated in either cm $H_2O$ or mmHg. The manometer tube 24 includes a connector 26 that is received within a funnel connector 28 formed on the urinary catheter 14 to provide fluid communication between the manometer tube 24 and the urinary catheter 14.

When the pressure measuring apparatus 10 of the present invention is in the draining position illustrated in FIG. 2, urine from the bladder 16 fills the reservoir 20 and overflow through an outlet opening 30 formed near the top end of an internal tube 34 positioned in the reservoir 20. The internal tube 34 includes a funnel connector 33 that receives a drainage tube 32 coupled to the collection container 18. Thus, the excess volume of urine from the reservoir 20 drains into the collection container 18, such that a constant volume is maintained in the reservoir 20.

The reservoir 20 includes an air vent 36 that vents the interior of the reservoir 20 to atmosphere. Specifically, the air vent 36 includes a hydrophobic filter and is placed in the top of the reservoir to allow sterile air to enter the reservoir in order to provide atmospheric pressure in the reservoir 20 while preventing contamination.

Figure 3:
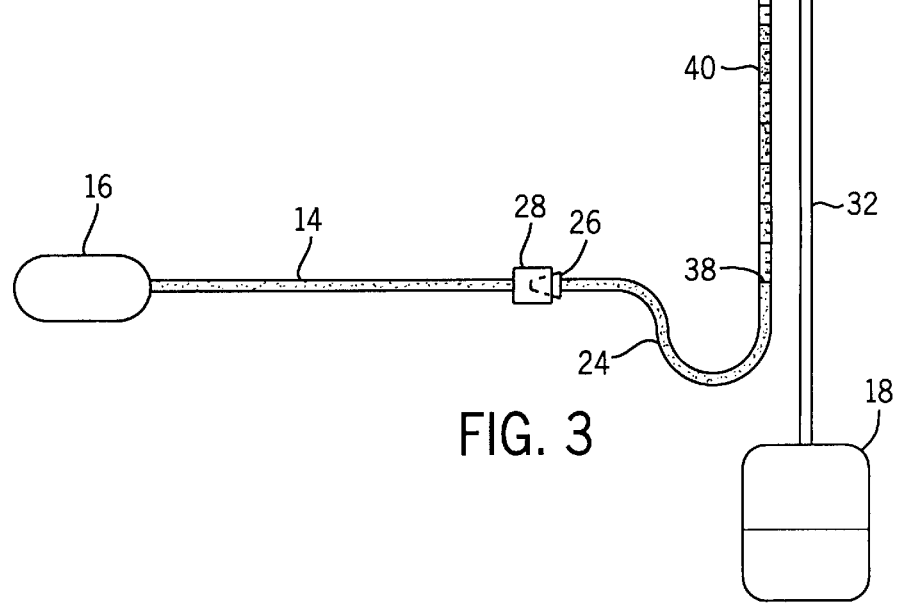
FIG. 3 is an illustration of the intra-abdominal pressure measuring device in its pressure measuring position.

Referring now to FIG. 3, thereshown is the intra-abdominal pressure measuring apparatus 10 of the invention in its elevated, measuring position. In the measuring position, the apparatus 10 can be used to determine the intra-abdominal pressure of the patient by returning the patient's own urine contained within the reservoir 20 back into the bladder 16.

The intra-abdominal pressure measurement is made by raising the reservoir 20 above the patient until a zero marking 38 on the manometer tube 24 is generally level with a horizontal axis extending through the pubic bone of the patient 12 when the patient is in the supine position. As the reservoir is being raised to the measurement height, gravitational forces cause the predetermined volume of urine to flow back into the patient's bladder.

Once the reservoir 20 has been elevated, the level of the urine within the manometer tube 24 reaches a level above the zero marking 38 that indicates the pressure within the bladder 16 of the patient. In FIG. 3, the level of the urine is indicated at line 40. As the reservoir 20 is raised to the elevated position shown in FIG. 3, the stored volume of urine in the reservoir 20 flows back into the patient's bladder 16 through the catheter 14 and the manometer tube 24. Since the specific gravity of urine is very close to 1.0, the bladder pressure is equivalent to the height of the urine contained within the manometer tube 24 above the zero marking. Again, the zero marking 38 positioned on a level with the horizontal axis extending through the pubic bone, and thus the bladder 16, within the patient 12.

In the preferred embodiment of the invention, the manometer tube 24 includes printed markings that are calibrated in either cm $H_2O$ or mmHg. The air vent 36 allows the pressure within the reservoir 20 to be maintained at atmosphere such that the manometer tube 24 provides an accurate measurement of the pressure within the bladder 16.

As can be illustrated in FIG. 3, the outlet opening 30 of the internal tube 34 is placed near the top of the reservoir 20. The position of the outlet opening 30 prevents the supply of bodily fluid within the reservoir 20 from draining into the collection container 18 through the drainage tube 32 as the reservoir 20 is elevated. Additionally, the outlet opening 30 is positioned such that the volume of the reservoir 20 is a known amount when the reservoir 20 is in its draining position, as illustrated in FIG. 2. In the preferred embodiment, of the invention, the reservoir 20 has a fixed volume of 50 cc, although a range of 5–100 cc is contemplated. The known volume of the reservoir 20 allows reproducible determinations to be made regarding the pressure within the patient's bladder 16.

Figure 4:
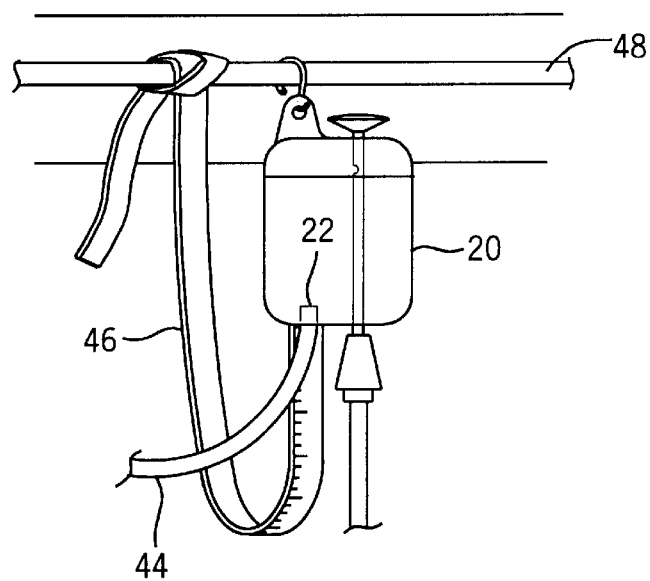
FIG. 4 is an illustration of an alternate configuration of the intra-abdominal pressure measuring device of the present invention.
Figure 5:
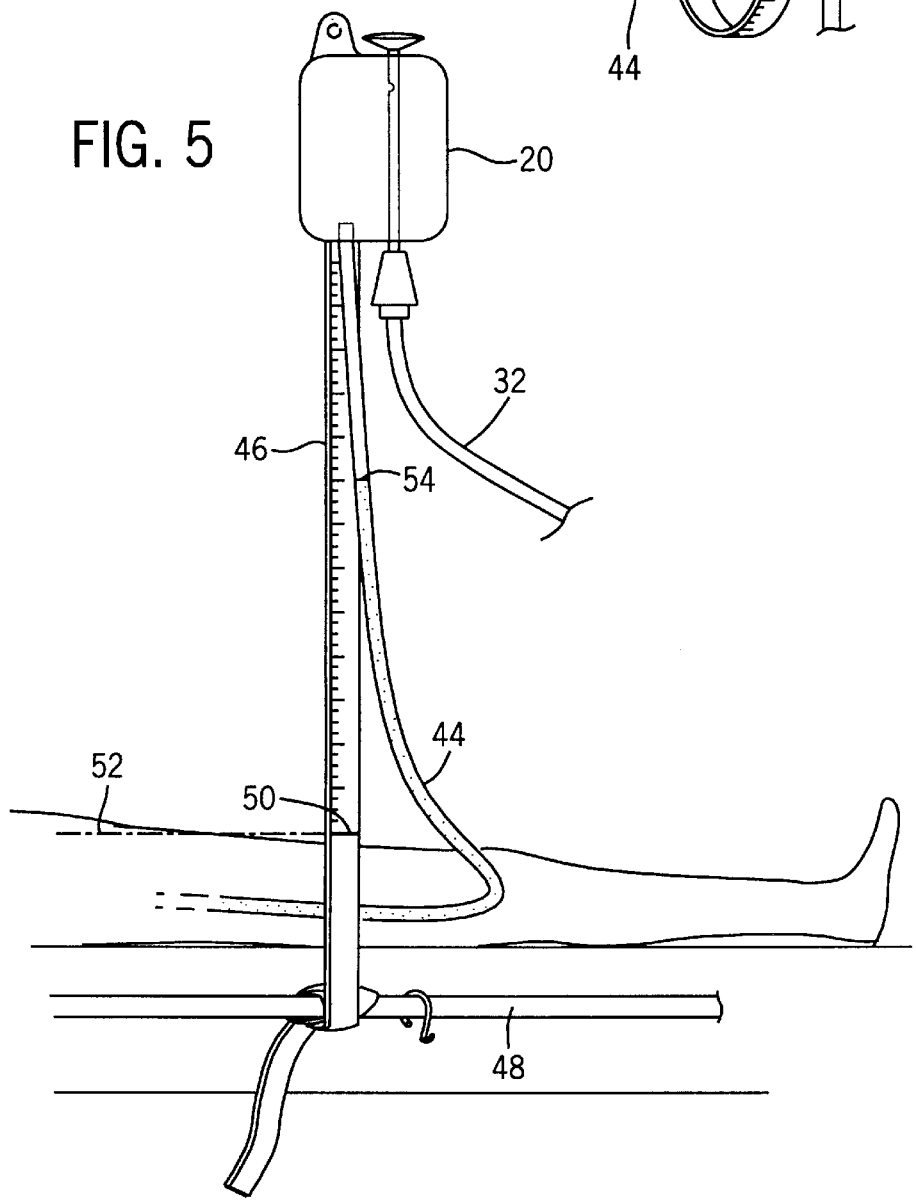
FIG. 5 is an illustration of the alternate configuration of the invention in its pressure measuring position.

Referring now to FIGS. 4 and 5, thereshown is an alternate configuration for the first embodiment of the invention. In the configuration illustrated in FIGS. 4 and 5, the inlet 22 to the reservoir 20 is connected to the urinary catheter by a transparent inlet tube 44, rather than the pre-marked manometer tube 24 illustrated in FIGS. 2–3. In the embodiment of the invention illustrated in FIG. 4, one end of a measuring tape 46 is attached to the reservoir 20. The opposite end of the measuring tape 46 is tied or otherwise fixed to a bed rail 48 or other component of the patient's bed in order to fix the length of the measuring tape 46 between the reservoir 20 and the bed rail 48.

As illustrated in FIG. 5, when the reservoir 20 is moved to its elevated, measuring position, the length of the measuring tape 46 restricts the upward movement of the reservoir 20 and defines the measurement height; Prior to being fixed to the bed rail, the length of the measuring tape 46 is adjusted until the zero marking 50 is level with the horizontal axis extending through the patient's pubic bone, as illustrated by the dashed line 52.

As was the case in the first embodiment of FIGS. 2 and 3, the level 54 of the bodily fluid within the inlet tube 44 can be measured by the markings on the measuring tape 46 to determine the intra-abdominal pressure within the patient.

In the first embodiment of the invention illustrated in FIGS. 1–5, the reservoir 20 is shown and described as being a separate component having an internal volume that stores a supply of the patient's urine that is returned to the patient's bladder during the intra-abdominal pressure measurement. However, it is contemplated by the inventor that the reservoir 20 could be replaced by an expanded diameter section of the inlet tube. The expanded diameter section of the inlet tube would be large enough to store a certain volume of urine, e.g., 5–10 cc, that would be returned to the patient during measurement of the intra-abdominal pressure. The expanded section of the inlet tube would include the air vent such that the inlet tube would be vented to atmosphere during the measurement of the intra-abdominal pressure.

Referring now to FIGS. 6–8, thereshown is a second embodiment of the present invention that is particularly useful in measuring the intra-abdominal pressure through the use of the pressure within a patient's stomach. As can be seen in FIG. 6, the pressure measuring apparatus 52 is connected to a catheter, such as a naso-gastric tube 56 that enters into the patient's stomach through the nasal cavity. Unlike the urinary catheter illustrated in the first embodiment of the invention, the fluids from the patient's stomach are typically removed by a suction device 58. The suction device 58 removes fluid from the patient's stomach and the fluid is stored within a collection container 60.

Referring now to FIG. 7, thereshown is the second embodiment of the reservoir 62. In FIG. 7, the reservoir 62 is shown in an inverted, draining position. In this position, a source of negative air pressure is supplied to the open interior of the reservoir 62 through a suction tube 64. The source of suction acts through an opening 66 contained within the internal tube 68 formed in the reservoir 62. As illustrated in FIG. 7, a ball 70 seals off the opening to an air vent 72 such that the supply of suction can remove stomach fluids through the naso-gastric tube 56.

In the second embodiment of the invention, the reservoir 62 is formed from rigid walls such that the suction generated through the suction tube 64 does not collapse the internal volume of the reservoir 62. In this manner, the reservoir 62 permits the suction device to operate properly to remove fluid from the patient's stomach.

Referring now to FIG. 8, thereshown is the reservoir 62 in its elevated, measuring position. As can be understood by comparing FIGS. 7 and 8, the reservoir 62 is moved from its inverted position shown in FIG. 7 to an upright position in FIG. 8.

When the reservoir 62 is in its upright position and elevated above the patient, as shown in FIG. 8, the internal volume of fluid in the reservoir drains through the manometer tube 74 and into the naso-gastric tube 56. As was the case in the first embodiment illustrated in FIGS. 2 and 3, the internal volume of the fluid contained within the reservoir 62 flows back into the patient's stomach. The reservoir 62 is elevated until the zero marking on the manometer tube 74 is generally at level with the pubic bone of the patient. When the reservoir 62 is positioned as such, the height of the fluid remaining within the manometer tube 74 can be measured by the external markings contained on the manometer tube 74. Thus, the intra-abdominal pressure of the patient can be measured by the height of the fluid contained within the manometer tube 74. As described previously, the preferred volume of the reservoir 62 is approximately 50 cc.

When the reservoir 62 is placed in its upright position, as shown in FIG. 8, the ball 70 falls down to block and the opening to the suction tube 64. In this manner, the ball 70 ensures that all of the volume of bodily fluid contained within the reservoir 62 enters into the manometer tube 74. A second opening 76 is formed in the internal tube 68 near the top of the internal tube 68 to allow the air vent 72 to maintain the interior of the reservoir 62 at atmospheric pressure.

Referring back to FIG. 7, the ball 70 also serves as a negative pressure regulator. For example, whether the reservoir 62 includes any bodily fluid or not, the weight of the ball 70 closes the air vent 72 which allows suction to be applied to the patient's stomach. The ball 70 will lift off of the seat to the air vent 72 when the amount of negative pressure within the reservoir is enough to physically lift the ball away from the air vent 72, allowing air to enter the reservoir, thus maintaining the negative pressure at a predetermined level. Thus, the weight of the ball 70 serves as a negative pressure regulator to prevent a large amount of negative pressure from being applied to the patient's stomach.

In addition to allowing the quick and easy measurement of intra-abdominal pressure of a patient, the pressure measuring apparatus of the present invention can also be used to check the patency of the drainage catheter. Presently, after a urinary catheter has been inserted into a patient for an extended period of time, the catheter may become partially or fully blocked by body product deposits that build up within the catheter tip drainage holes or in the lumen. This phenomenon is referred to as "incrustation".

When the pressure measuring apparatus of the present invention is moved to its elevated, measuring height, a partially or fully blocked catheter can be "diagnosed" by the speed at which the reservoir empties into the bladder. For example, very slow emptying of the reservoir into the bladder indicates a blocked or partially blocked catheter that must be replaced. However, if the reservoir drains into the bladder rapidly, this is an indication that the catheter is functioning normally. Since the patient's own urine is being returned to the bladder, checking the catheter for incrustation can be done quickly and easily with little to no additional risk of infection.

Various alternatives and embodiments are contemplated as being within the scope of the following claims particularly pointing out and distinctly claiming the subject matter regarded as the invention.

I claim:

1. A method of determining the intra-abdominal pressure in a patient having a catheter that drains fluid from the patient into a collection container, the method comprising the steps of:

positioning a reservoir between the catheter and the collection container, the reservoir being connected to the catheter by a transparent inlet tube such that the reservoir fills with the fluid drained from the patient when the reservoir is positioned below the patient;

raising the reservoir to a defined measurement height above the patient such that the volume of the fluid in the reservoir flows back into the patient through the transparent inlet tube and the catheter; and measuring the height of the fluid in the transparent inlet tube after the fluid has been returned to the patient from the reservoir to determine the intraabdominal pressure in the patient.

2. The method of claim 1 wherein the transparent inlet tube includes a zero marking, wherein the step of raising the reservoir above the patient includes raising the reservoir until the zero marking on the transparent inlet tube is level with a horizontal axis extending through the patient such that the height of the volume of fluid in the transparent inlet tube is measured from the zero marking.

3. The method of claim 2 wherein the horizontal axis of the patient is the level of the pubic bone when the patient is in a supine position.

4. The method of claim 1 further comprising the step of venting the reservoir to atmosphere prior to raising the reservoir above the patient.

5. The method of claim 1 further comprising the step of blocking the flow of bodily fluid to the collection container prior to raising the reservoir to the measurement height.

6. The method of claim 1 further comprising the step of filling the reservoir to a predetermined measurement volume prior to the reservoir being raised to the measurement height.

7. The method of claim 6 further comprising the step of allowing the fluid to overflow from the reservoir to the collection container when the volume of fluid in the reservoir exceeds the measurement volume.

8. The method of claim 1 further comprising the steps of:

connecting the reservoir to a source of negative pressure such that the source of negative pressure draws the fluid from the patient into the reservoir;

providing an air vent in the reservoir such that when the air vent is open, the interior of the reservoir is maintained at atmospheric pressure;

blocking the air vent when the reservoir is positioned below the patient; and opening the air vent to vent the reservoir to atmosphere when the reservoir is at the measurement height.

9. A device for determining the intra-abdominal pressure in a patient having a catheter for draining fluid from the patient into a collection container, the apparatus comprising:

a reservoir having an inlet and an outlet;

a transparent inlet tube connecting the inlet of the reservoir to the catheter such that the fluid from the patient drains into the reservoir through the inlet tube when the reservoir is below the patient and fluid from the reservoir flows back to the patient when the reservoir is positioned above the patient;

a drainage tube connecting the outlet of the reservoir to the collection container, wherein fluid for the reservoir overflows into the discharge tube through the outlet;

an air vent formed in the reservoir such that the interior of the reservoir is vented to atmospheric pressure when the air vent is in an open position;

a measurement height indicator associated with the inlet tube, wherein the measurement height indicator determines a measurement height of the reservoir above the patient, the measurement height being used to determine the intra-abdominal pressure; and a liquid level indicator associated with the inlet tube to indicate the height of the liquid in the inlet tube when the reservoir is at the measurement height.

10. The device of claim 9 wherein the liquid level indicator is a series of markings formed on the transparent inlet tube, the markings being spaced from each other to represent the intra-abdominal pressure in the patient.

11. The device of claim 9 wherein the liquid level indicator is a measuring tape having a first end fixed to the reservoir and a second end fixed relative to the patient, wherein the measuring tape includes a series of markings such that when the reservoir is at the measurement height, the markings on the measurement tape are positioned near the transparent inlet tube.

12. The device of claim 9 wherein the measurement height indicator is a zero marking printed on the inlet tube, wherein the measurement height is reached when the zero indicator is level with a horizontal axis extending through the patient.

13. The device of claim 11 wherein the measurement height indicator is a zero marking printed on the measurement tape such that the measurement height is reached when the zero marking is level with a horizontal axis extending through the patient.

14. The device of claim 9 further comprising a closing device positioned to prevent the flow of fluid through the drainage tube when the reservoir is in an upright position.

15. The device of claim 14 wherein the closing device blocks the air vent when the reservoir is in an inverted position.

16. The device of claim 9 wherein the outlet for the reservoir is positioned such that once the volume of liquid in the reservoir reaches a predetermined measurement volume, additional fluid flowing into the reservoir overflows the reservoir through the outlet opening such that the reservoir maintains the constant measurement volume.

17. The device of claim 9 wherein the air vent includes a filter to prevent contamination of the fluid within the reservoir.

18. A method of determining the intra-abdominal pressure in a patient having a catheter that drains fluid from the patient into a collection container, the method comprising the steps of:

positioning a reservoir between the catheter and the collection container, the reservoir being connected to the catheter by an inlet tube such that the reservoir fills with the fluid drained from the patient when the reservoir is positioned below a horizontal axis extending through the abdominal cavity of the patient when the patient is a supine position;

allowing the reservoir to fill with the fluid from the patient until the volume of fluid overflows through an outlet formed in the reservoir, such that a measurement volume of fluid is contained within the reservoir;

raising the reservoir to a measurement height above the horizontal axis passing through the patient such that the measurement volume of fluid in the reservoir flows back into the patient through the inlet tube and the catheter; and measuring the height of the fluid in the inlet tube above the horizontal axis when the reservoir is at the measurement height, the height of the fluid in the inlet tube being indicative of the intra-abdominal pressure in the patient.

19. The method of claim 18 wherein the inlet tube is transparent and includes a zero marking, wherein the step of raising the reservoir above the patient to the measurement height includes raising the reservoir until the zero marking on the inlet tube is level with the horizontal axis of the patient.

20. The method of claim 18 further comprising the step of venting the reservoir to atmosphere when the reservoir is positioned at the measurement height.

21. The method of claim 18 further comprising the step of preventing the flow of fluid from the reservoir to the collection container as the reservoir is raised to the measurement height.

* * * * *